(12) United States Patent
Shizuno et al.

(10) Patent No.: US 7,137,165 B2
(45) Date of Patent: Nov. 21, 2006

(54) ADHESIVE ROLL CLEANER

(75) Inventors: Akihito Shizuno, Tochigi (JP); Takehiko Uematsu, Tochigi (JP)

(73) Assignee: KAO Corporation, Tokyo (JP)

( * ) Notice: Subject to any disclaimer, the term of this patent is extended or adjusted under 35 U.S.C. 154(b) by 97 days.

(21) Appl. No.: 10/373,961

(22) Filed: Feb. 27, 2003

(65) Prior Publication Data

US 2003/0167583 A1    Sep. 11, 2003

(30) Foreign Application Priority Data

| Feb. 28, 2002 | (JP) | ............................. 2002-054468 |
| Dec. 10, 2002 | (JP) | ............................. 2002-357861 |
| Feb. 20, 2003 | (JP) | ............................. 2003-043273 |

(51) Int. Cl.
*A47L 25/00* (2006.01)

(52) U.S. Cl. .................... 15/104.002; 15/48; 428/343; 428/354

(58) Field of Classification Search ........... 15/104.002, 15/41.1, 48; 428/343, 354
See application file for complete search history.

(56) References Cited

U.S. PATENT DOCUMENTS

| 3,342,325 A | * | 9/1967 | Dreher | ........................ 206/400 |
| 3,417,418 A | * | 12/1968 | Ribound | ................. 15/104.002 |
| 4,103,382 A | | 8/1978 | Gitt | |
| 5,256,234 A | | 10/1993 | Mutaguchi et al. | |
| 5,548,861 A | | 8/1996 | Hukuba | |
| 5,763,038 A | * | 6/1998 | Wood | .......................... 428/43 |
| 6,030,674 A | | 2/2000 | Onishi et al. | |

FOREIGN PATENT DOCUMENTS

| EP | 1304069 A2 | 4/2003 |
| JP | 3-10853 U | 2/1991 |
| JP | 6-264038 A | 9/1994 |
| JP | 8-126602 A | 5/1996 |
| JP | 9-173276 A | 7/1997 |
| JP | 10-5159 | * 1/1998 |
| JP | 11-216096 A | 8/1999 |
| JP | 2001-383 A | 1/2001 |
| JP | 2001-234148 A | 8/2001 |
| JP | 3081512 U | 8/2001 |

* cited by examiner

*Primary Examiner*—Gladys JP Corcoran
*Assistant Examiner*—Abraham Bahta
(74) *Attorney, Agent, or Firm*—Birch, Stewart, Kolasch & Birch, LLP

(57) ABSTRACT

An adhesive roll cleaner having a single-sided adhesive sheet wound around a core tube into a roll with the adhesive side facing out, wherein the adhesive sheet has a tear strength of 500 mN or higher and is wound in such a manner that the adhesive roll cleaner maintains an outer diameter within a range of 22 to 40 mm from start to end of use, and the roll has a width of 180 to 300 mm.

4 Claims, 5 Drawing Sheets

ADHESIVE ROLL CLEANER

This application claims the priority of Japanese Patent Application Nos. 2002-54468 filed Feb. 28, 2002, 2002-357861 filed Dec. 10, 2002 and 2003-43273 filed Feb. 20, 2003 which are incorporated herein by reference.

BACKGROUND OF THE INVENTION

The present invention relates to a roll type adhesive cleaner used to clean carpeted or non-carpeted floors.

Adhesive roll cleaners generally used to clean floors or carpets usually measure 40 mm in minimum diameter, 50 to 60 mm in maximum diameter, and 160 mm in roll width and have about 90 to 100 turns of an adhesive sheet wound around the core. Reference can be made to, e.g., JP-A-2001-383. Because of their outer diameters, adhesive roll cleaners of these sizes are difficult to insert into the clearance under castered furniture such as an upright piano or furniture with a raised base. Where the furniture is placed on a deep pile carpeted floor, the clearance space under the furniture is even narrower. Thus, a user inserts the roll into the space, it is not easy to move the roll cleaner. Therefore, if a user utilizes the roll cleaner in such a space, the furniture must be moved to clean the floor under the furniture, which makes it difficult to give rooms a thorough cleaning.

A reduction of the diameter of the adhesive roll is a conceivable approach to eliminate the above-mentioned inconveniences. However, a reduction of the diameter means a reduction of the adhesive surface area, i.e., the area of a single turn of the adhesive sheet. It thus naturally follows that the frequency of removing a soiled portion of the adhesive sheet increases to an undesirable degree. Further, an adhesive roll cleaner with a reduced diameter tends to collect hair winding in many turns therearound such that a soiled adhesive sheet is apt to be torn apart by the twining hair as it is peeled.

SUMMARY OF THE INVENTION

An object of the present invention is to provide a compact and manageable adhesive roll cleaner which has a reduced diameter so as to be capable of cleaning the floor with a narrow clearance under furniture and also at corners of a room while exhibiting satisfactory dust collecting ability and sufficient cleaning performance sustainability (cleanable area per peel).

Another object of the present invention is to provide an adhesive roll cleaner the outermost layer of which, when soiled, is easily peeled off without being torn by twining fibrous dust, e.g., hairs.

The above objects are accomplished by an adhesive roll cleaner having a single-sided adhesive sheet wound around a core tube into a roll with the adhesive side facing out, wherein the adhesive sheet has a tear strength of at least 500 mN and is wound in such a manner that the adhesive roll cleaner maintains an outer diameter and width from start to end of use which renders it effective for cleaning in small clearance spaces. In a preferred embodiment of the present invention where the adhesive strength of the roll surface falls within a specific range, the adhesive roll cleaner of the present invention exhibits effective cleaning performance, even with a reduced diameter as never seen before.

BRIEF DESCRIPTION OF THE DRAWINGS

The present invention will be more particularly described with reference to the accompanying drawings, in which.

DETAILED DESCRIPTION OF THE PREFERRED EMBODIMENTS

Figure 1:
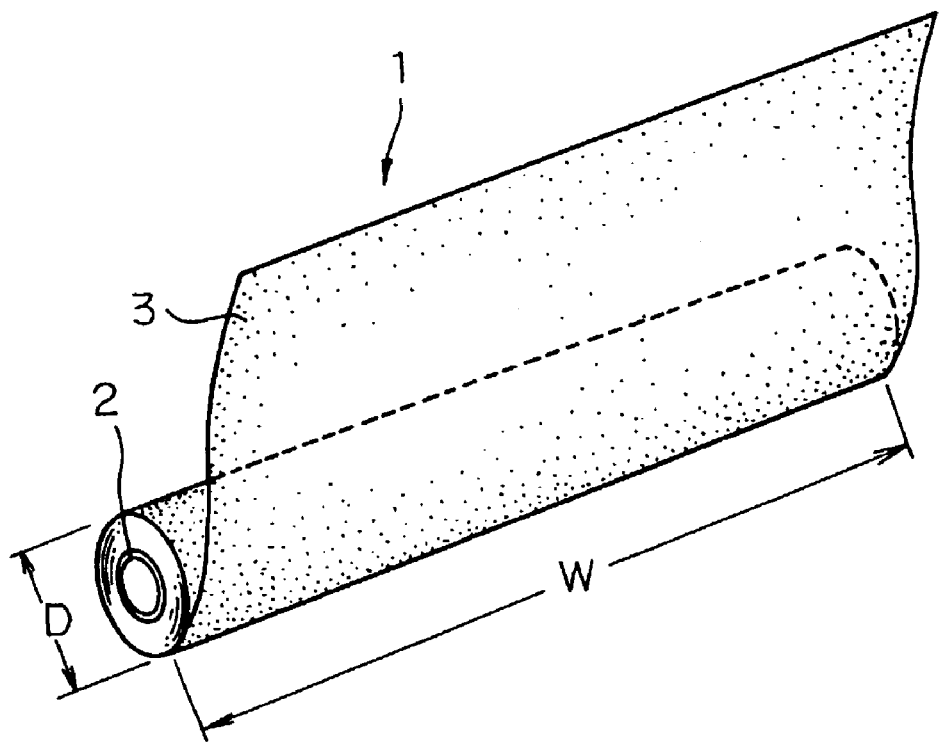
FIG. 1 is a perspective view showing an embodiment of the adhesive roll cleaner according to the present invention.

The present invention will be described in detail based on its preferred embodiments with reference to the accompanying drawings. FIG. 1 is a perspective view of an embodiment of the adhesive roll cleaner (or simply "roll cleaner") according to the present invention. The adhesive roll cleaner 1 is composed of a cylindrical core tube 2 and an adhesive sheet 3 of continuous length wound around the core tube 2 with edges even. The adhesive sheet 3 is made of a base sheet having an adhesive applied all over one side thereof, which is referred to as a single-sided adhesive sheet. The other side of the adhesive sheet 3 has a release finish against the tack. The adhesive sheet 3 is wound around the core tube 2 with its adhesive side facing out. The adhesive sheet 3 has perforations which extend over the whole width at regular intervals in the longitudinal direction. The perforations may be replaced with notches at the edge, from which a soiled part of the adhesive sheet can be torn off.

The roll cleaner 1 has an adhesive surface over its whole width. On rolling the roll cleaner 1 on a surface to be cleaned, the adhesive surface catches up dust from the surface to be cleaned. Each time a quantity of dust adheres to the adhesive surface, the soiled outermost layer of the adhesive sheet 3 is peeled off and torn apart along the perforations to expose a fresh adhesive surface. Accordingly, the roll cleaner 1 is gradually reduced in outer diameter with use. In the present invention, the adhesive sheet 3 is wound to such an extent that the outer diameter D of the roll cleaner 1 (see FIG. 1) may be preferably maintained within a range of from 22 to 40 mm, more preferably from 23 to 38 mm, during use. In other words, the roll cleaner 1 preferably has an outer diameter D in that range from the start to the end of use. It should be noted that the above-recited range of D is smaller than that of ordinary adhesive roll cleaners.

In the present invention, the roll cleaner 1 preferably has a width W (see FIG. 1) of 180 to 300 mm, more preferably 190 to 250 mm. As shown in FIG. 1, the roll width W in the present embodiment is equal to the width of the adhesive surface. That is, the adhesive surface is preferably 180 to 300 mm wide, more preferably 190 to 250 mm wide. Note that the width W of the adhesive surface is greater than that of ordinary adhesive roll cleaners.

While in the embodiment shown in FIG. 1 the adhesive surface is provided over the whole width of the roll, 3 to 6 mm wide portions extending from both edges of the roll may remain uncoated with an adhesive. In this case, a user picks up the non-adhesive edge to peel off the soiled adhesive sheet without soiling his or her hand.

While in the embodiment shown in FIG. 1 the adhesive is applied uniformly over the entire area of the adhesive sheet 3, the adhesive may be applied in a stripe pattern alternating adhesive portions with 1 to 3 mm wide of non-adhesive or little adhesive portions across the longitudinal direction. With this design, the roll cleaner 1 has moderately reduced adhesive strength as a whole while maintaining a high dust trapping performance in parts so that it is prevented from too strongly sticking to a surface to be cleaned thereby enabling the roll cleaner to be rolled with ease.

A roll with the combination of an outer diameter D and a width W within the above-recited respective ranges provides a roll cleaner which exhibits effective dust collecting performance and effective cleaning performance sustainability (a cleanable area per peel) and yet is compact and sufficiently manageable to clean the floor under a furniture with narrow clearance and also at corners of a room. Failure to satisfy either one of the dimensional requirements prevents the object of the present invention from being accomplished. For example, if the outer diameter D exceeds 40 mm and/or if the width W exceeds 300 mm, it is difficult to clean narrow spaces under furniture or at corners of a room. If the outer diameter D is smaller than 22 mm, the roll cleaner has insufficient dust collecting performance or insufficient cleaning performance sustainability for an efficient cleaning operation. If the width W is smaller than 180 mm, sufficient dust collecting performance is not obtained unless the outer diameter is increased, or a user must peel off the soiled portion very frequently.

The outer diameter D and the width W of the roll cleaner 1 are measured with a vernier caliper. In putting the roll cleaner 1 between jaws of a vernier caliper, care should be taken not to deform the roll cleaner 1.

As stated supra, the roll cleaner 1 has a greater width and a smaller outer diameter than ordinary rolls. Therefore, when a soiled part of the adhesive sheet 3 is peeled off with long fibrous dust, such as hair clinging thereto in the circumferential direction, it is more likely that the adhesive sheet 3 is torn apart by the twining hair rather than with smaller roll widths. Further, fibrous dust such as a hair is apt to twine around the roll more times than on rolls with usual outer diameters, causing the adhesive sheet 3 to be torn more easily. In order to prevent such an inconvenience, the adhesive sheet 3 should have a tear strength of 500 mN or higher as measured with an Elmendorf tear tester (hereinafter referred to as an Elmendorf tear strength or, simply, a tear strength) according to JIS P8116. It is preferred for the adhesive sheet 3 to have an Elmendorf tear strength of 600 mN or greater, particularly 800 mN or greater. Where the adhesive sheet 3 has this Elmendorf tear strength in its longitudinal direction, tearing caused by twining hair, etc. is effectively prevented. The upper limit of the tear strength is not particularly limited. The higher the tear strength, the more preventive it is for the adhesive sheet 3 from being torn due to twining hair. From the economical consideration, however, the practically preferred upper limit of the tear strength is about 100 N.

The Elmendorf tear strength of the adhesive sheet 3 is measured as follows.

(a) Preparation of the Specimen and Method of Measurement

The procedure of JIS P8116 (ISO 1974) is followed. In this particular measurement the tear strength of an adhesive sheet in the longitudinal direction, i.e., the machine direction (MD) is measured. A plurality of test specimens 63 mm wide (in MD) and 75 mm long (in CD) cut out of a sample are stacked, with the release-finished side and the adhesive side facing each other to give a measurement within an effective measurement range, which is between scale readings 0 gf and 100 gf, desirably 25 gf and 100 gf, on an Elmendorf tear tester. When the specimens are stacked, the adhesive side is liable to stick to the releasable side. Because JIS P8116 specifies that the stacked specimens must not stick together, the specimens need pretreatment for eliminating the tackiness of the adhesive. This can be done by uniformly applying silicone powder (KMP590, Lot 712180, available from Shin-Etsu Chemical Co., Ltd.) to the adhesive surface with a 30 mm wide brush. Surface unevenness due to powder application is suppressed to some extent by the use of a brush. The amount of silicone powder to be applied is such that the adhesive-coated side of the adhesive sheet becomes tack-free as ascertained by applying finger pressure. As the pretreatment is intended to eliminate the tack of the adhesive sheet, any other commercially available powder may be used for the pretreatment. The stack of the specimens is secured between two clamps with the width direction of the specimens (MD of the adhesive sheet) positioned vertically and the length direction (CD of the adhesive sheet) positioned horizontally. A 20 mm long initial tear is vertically made at the middle of the length (CD) from the lower edge of the stack with the attached cutter. The tester is operated according to JIS P8116. On confirming complete vertical tear propagation across the width (MD), the load (gf) required for tearing is determined. The measurement was repeated several times for example quadruplicated for the same sample to ensure reproducibility.

(b) Data Analysis

The resulting data are converted to an Elmendorf tear strength F of a stack of 16 specimens as specified in JIS P8116 according to the following formula:

$$\text{Tear strength } F(mN) = W(gf)/n \times 16 \times g \text{ (m/s}^2\text{)}$$

where W (gf) is the reading of an Elmendorf tear tester; n is the number of specimens stacked; and g is an acceleration of gravity (=9.8 (m/s$^2$))

An average of the quadruplicate measurements is taken as the tear strength of the sample. Since the tear strength is a 16-specimens-equivalent value, it is believed that a difference in the number of specimens stacked for each sample has no influence on the results.

JIS P8116 specifies a 63 mm wide specimen in the measurement of the tear strength. In case the width of an actual specimen is less than 63 mm, the data obtained are normalized to a 63 mm width. More specifically, JIS P8116 specifies that a 20 mm long initial tear be made in a 63 mm wide specimen so that the tear length may be 43 mm. If the width of an actual specimen is 50 mm for example, the actual tear length is (50-20) mm, i.e., 30 mm. Then, the tear strength as defined in JIS P8116 is obtained by multiplying the measured tear strength by 43/30.

The adhesive sheet 3 with the above-recited tear strength can be obtained by, for example, appropriately selecting the material and/or the basis weight (or coating weight) of the base sheet or the adhesive applied. As for the base sheet, useful sheet materials include paper, films of plastics, such as polyester, polyolefines, e.g. polypropylene, and non-woven fabric. Paper is preferred from the standpoint of workability in applying an adhesive and in winding the adhesive sheet 3, production cost, and the like. Paper which can be used as a base sheet includes grassine paper, pure white paper, kraft paper, and the like.

The tear strength of paper can be heightened by, for example, (1) increasing the total number of fibers participating in the breakage of the sheet or (2) selecting the kind of the pulp (e.g., length or thickness of the fibers). In the method (1), the total number of fibers participating in breakage of the sheet is decided by the basis weight of paper and flexibility of the sheet. Paper with a larger basis weight or paper with higher flexibility has a greater total number of fibers participating in sheet breakage and exhibits a higher tear strength. Methods for increasing flexibility of paper include Culpak processing and creping. In the method (2), higher tear strength can be obtained by using pulp fibers having a long fiber length, pulp fibers having a thick diameter, pulp fibers having a considerably thick fiber wall, or like pulp fibers in a larger proportion. The work of tearing paper involves the work of drawing fibers from paper and the work of breaking the fibers. The work necessary to draw the fibers is far greater than the work necessary to break the fibers. Accordingly, soft wood pulp having a long fiber length is preferred. Of soft wood pulp kinds, those with a longer fiber length are more effective to increase the tear strength. Tear strength of paper can also be improved by making paper from wood pulp mixed with other fibers such as glass fiber or by adding an elastic polymer such as synthetic rubber. However, use of pulp fiber having a long fiber length or an increase of the basis weight results in increased paper stiffness, and it would follow that the resulting adhesive sheet is difficult to wind at a small radius. From these considerations it is preferred that paper to be used as a base sheet be flexible particularly in the winding direction, i.e., in the longitudinal direction of the adhesive sheet. Such paper includes the above-described Culpak-processed extensible paper. Paper used as a base sheet preferably has a basis weight of 40 to 200 g/m$^2$, particularly 50 to 100 g/m$^2$.

Tear strength of paper can also be enhanced by laminating with a synthetic resin film either by extrusion or bonding. In this case, the thickness (e.g., 25 μm or greater) of the resin film or the kind of the laminating resin should be selected appropriately.

Figure 2:
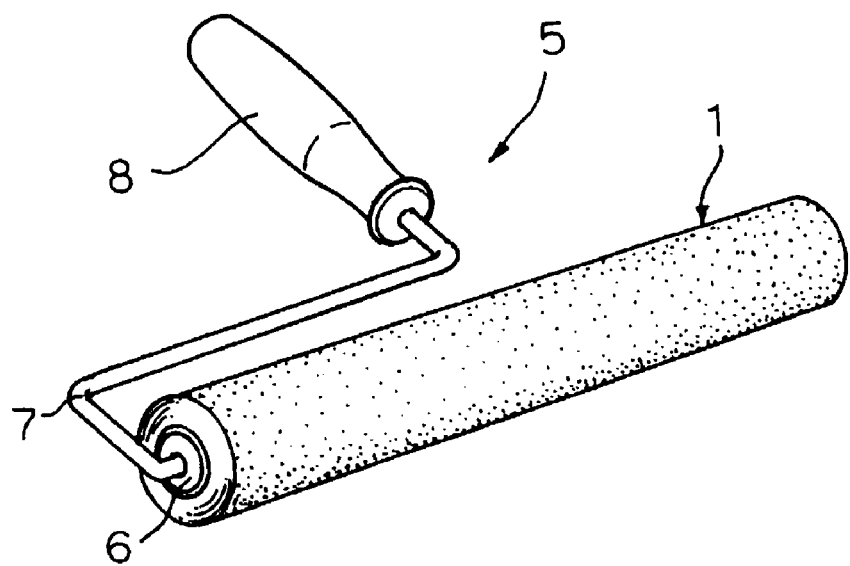
FIG. 2 shows an application of the adhesive roll cleaner of FIG. 1.
Figure 3:
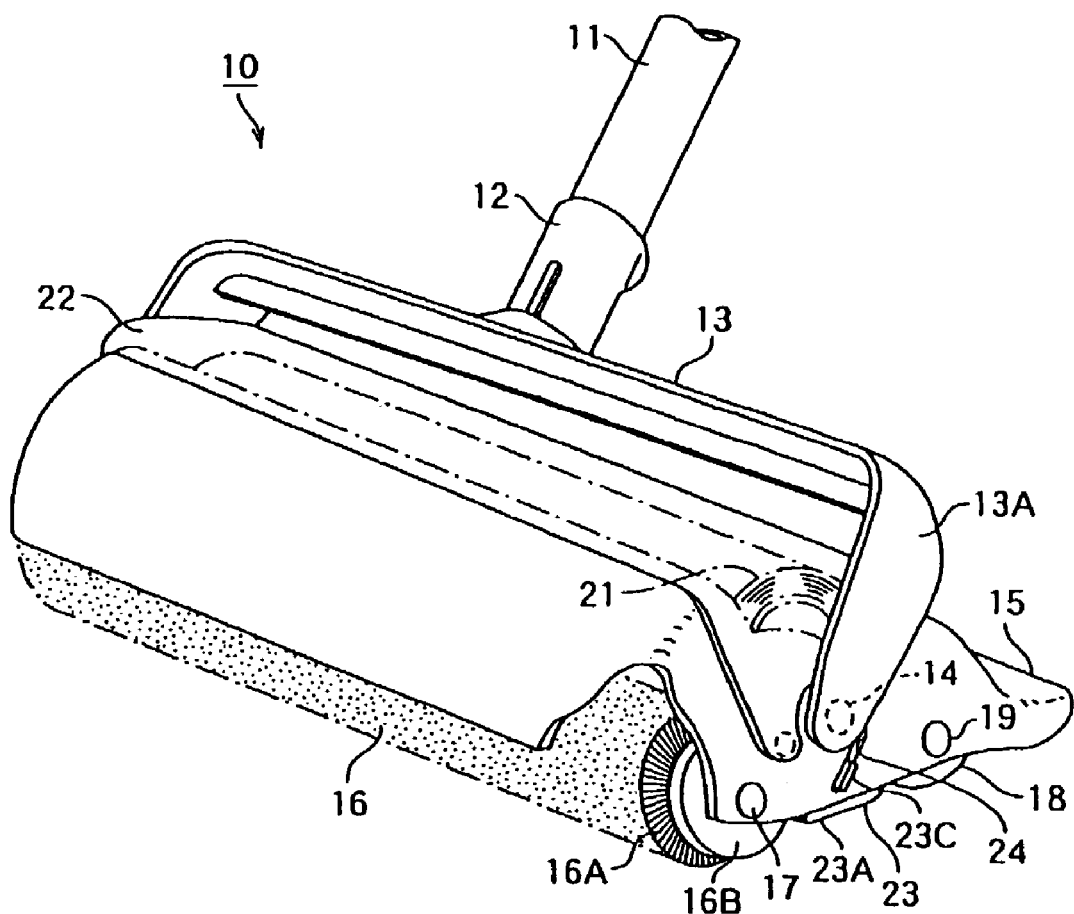
FIG. 3 shows another application of the adhesive roll cleaner of FIG. 1.
Figure 4:
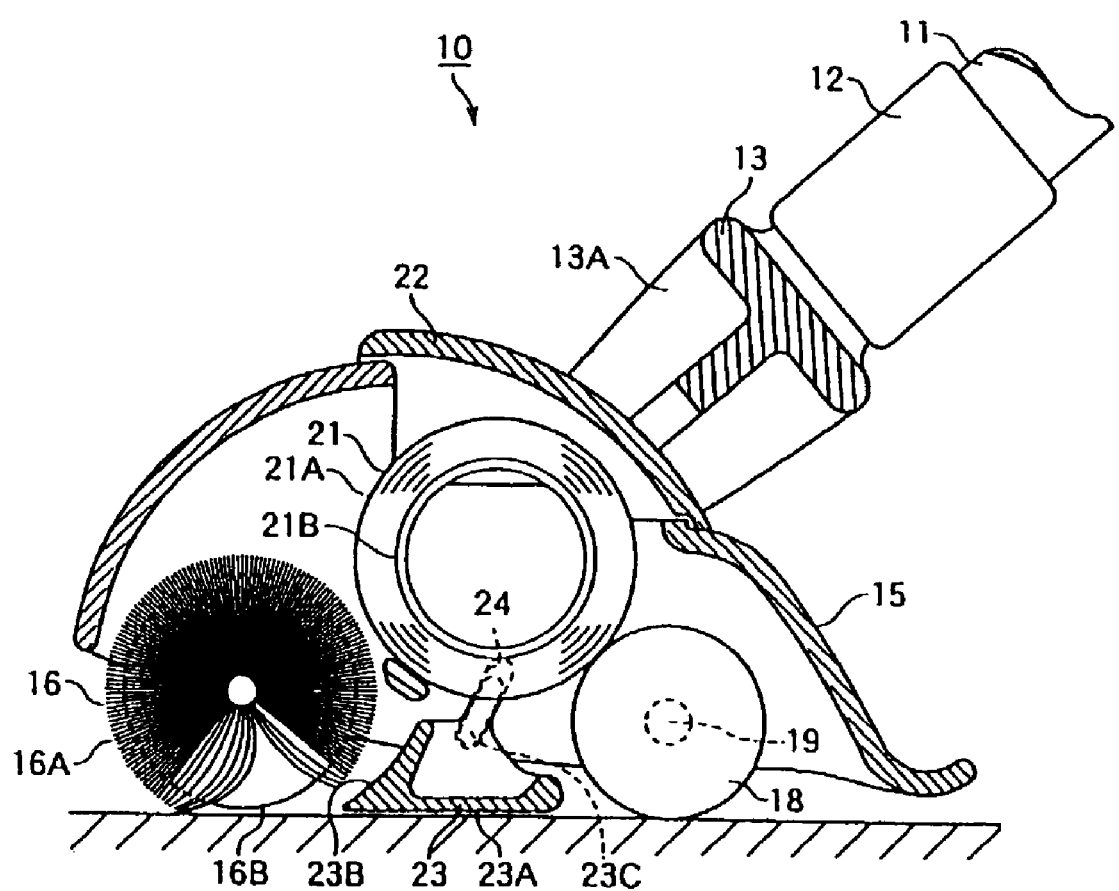
FIG. 4 is a side sectional view of FIG. 3.

The adhesive sheet 3 preferably has a rolling ball tack of 11 to 30, particularly 12 to 25, especially 14 to 25, on its adhesive side as measured in accordance with JIS Z0237-2000. With this tack, the adhesive sheet 3 shows sufficient dust catching and holding power and is free from the problem that the tack reduces with the adherence of a small amount of dust. A rolling ball tack of 11 or greater is preferred, especially considering that the adhesive sheet 3, having come to be soiled after some use, drastically loses its ability to catch dust such as a hair. With this rolling ball tack, even though the roll cleaner 1 has a reduced outer diameter and a corresponding reduced adhesive surface area, sufficient cleaning performance still (a cleanable area per peel) can be secured. With a rolling ball tack of 30 or smaller, the adhesive roll cleaner 1 assures satisfactory manageability in use. If the rolling ball tack of the adhesive sheet exceeds 30, the adhesive roll cleaner 1 can pluck piles causing damage to carpeting when used as an attachment to a direct contact type cleaning tool as shown in FIG. 2 (described later). Also, the adhesive roll cleaner 1 tends to be sticky to the user's hand which impairs manageability when used as an attachment to an indirect contact type cleaning tool, as shown in FIGS. 3 and 4 (described later).

The rolling ball tack is measured according to JIS Z0237 (Testing methods for adhesive tapes and sheets) as follows.

A specimen cut out of an adhesive sheet sample is set (the adhesive side up) on an inclined plate of a ball rolling tool. The angle of the plate is set at 30°. Balls of increasing sizes are rolled one by one at a specified position above the specimen. Balls of 31 sizes from $\frac{1}{16}$ to $\frac{16}{16}$ except $\frac{5}{64}$, $\frac{7}{64}$, $\frac{9}{64}$, $\frac{15}{64}$, and $\frac{17}{64}$ of nominal diameter specified in JIS B1501 (a 32 multiple of the nominal size is called a ball number) are used (first rolling). The biggest ball stopped on the specimen, a ball one size bigger than that biggest ball, and a ball one size smaller than that biggest ball are again rolled (second rolling) to confirm that the biggest ball stopped on the specimen in the first rolling is really the biggest one meeting the specification of measurement. The tack of the specimen is represented by the ball number of the biggest ball stopped on the specimen. An average of triplicate runs is taken as the rolling ball tack of the sample according to JIS Z0237.

The kind and the amount of the adhesive applied to the base sheet are selected so that the rolling ball tack may fall within the above-recited range. The adhesives which are preferably used include hot-melt adhesives, solvent adhesives, and aqueous adhesives. The hot-melt adhesives include styrene-based adhesives and olefin-based adhesives. The solvent adhesives include styrene-based, olefin-based, or acryl-based adhesives. The aqueous adhesives include acrylic adhesives. Use of styrene-based hot-melt adhesives will make it easy to obtain a rolling ball tack within the above range.

The hot-melt adhesives preferably comprise a base polymer, a tackifier, a softener, and an antioxidant. The base polymer includes styrene-butadiene rubber (SBR), a styrene-butadiene-styrene block copolymer (SBS), a styrene-isoprene-styrene block copolymer (SIS), a styrene-ethylene-butylene-styrene block copolymer (SEBS), and a styrene-ethylene-propylene-styrene block copolymer (SEPS). The base polymer is usually used in an amount of 10 to 100 parts by weight per 100 parts by weight of the total of the tackifier and the softener.

The tackifier includes $C_5$ monomer-based petroleum resins, $C_9$ monomer-based petroleum resins, dicyclopentadiene-based petroleum resins, rosin-based petroleum resins, polyterpene resins, and terpene phenol resins. The tackifier is usually used in an amount of 50 to 90 parts by weight per 100 parts by weight of the total of the tackifier and the softener.

The softener includes process oil, mineral oil, various plasticizers, polybutene, and liquid tackifying resins, each having a softening point of 10° C. or lower and an average molecular weight of 200 to 700. It is usually used in an amount of 10 to 50 parts by weight per 100 parts by weight of the total of the tackifier and the softener.

The antioxidant includes phenol antioxidants, amine antioxidants, phosphorus antioxidants, and benzimidazole antioxidants. It is usually used in an amount of 0.5 to 3 parts by weight per 100 parts by weight of the total of the tackifier and the softener.

The hot-melt adhesive can contain other components commonly used in adhesives.

The adhesive is preferably applied to a coating weight of 15 to 50 g/m$^2$, particularly 25 to 40 g/m$^2$. This coating weight is preferred for easily achieving the above-recited range of rolling ball tack and for preventing the adhesive from being pressed out of the roll edge, especially when the roll cleaner is placed in a 30° C. or higher temperature environment for a long period of time.

It is preferred to apply a silicone release agent to the back side of the adhesive sheet 3. It is preferred for some kinds of the base sheet to be laminated with low-density polyethylene for surface filling before the application of the release agent.

The diameter of the core tube used in the present invention is decided so that the outer diameter D of the roll cleaner 1 may not deviate from the range specified in the invention.

The roll cleaner 1 according to the present embodiment can be used as an attachment to a conventional J-roller holder, such as the one shown in FIG. 2. In this application, the adhesive surface of the roll cleaner 1 comes into direct contact with the surface to be cleaned. The J-roller holder 5 shown in FIG. 2 has a roller 6 which holds the roll cleaner 1, an arm 7 which supports the roller 6, and a handle 8 which extends from the rear end of the arm 7. Taking the outer diameter D of the roll cleaner 1 into consideration, the roller 6 is preferably 20 to 30 mm, particularly 20 to 26 mm, in diameter. The width of the roller 6 is preferably 180 to 300 mm, still preferably 190 to 250 mm, for assuring manageability in cleaning a floor under narrow clearances and at corners of a room.

While the roll cleaner 1 according to the present embodiment is suited to clean a floor under narrow clearances and at the corners of a room as previously mentioned, it is useful as well for the ordinarily cleaning of floors, as a matter of course. For this application, the roll cleaner 1 is preferably attached to a cleaning tool shown in FIGS. 3 and 4. In this case, the adhesive surface of the roll cleaner 1 is in indirect contact with the surface to be cleaned. The cleaning tool 10 of FIGS. 3 and 4 has a brush roll 16 and a driving roll 18 which are disposed in parallel to each other and rotatably supported by a frame 15, and an adhesive roll 21 which bridges the distance between the brush roll 16 and the driving roll 18. The adhesive roll cleaner according to the present embodiment is used as the adhesive roll 21. The cleaning tool 10 will now be described in more detail.

The cleaning tool 10 comprises a handle 11, a supporting arm 13 which is laterally, pivotably connected to the tip of the handle 11 via a joint 12, and the frame 15 which is pivotably connected to the side arms 13A of the supporting arm 13 through pivots 14 so as to swing back and forth.

The brush roll 16 is rotatable on its rotating shaft 17 and supported in front of the frame 15. The driving roll 18 is rotatable on its rotating shaft 19 and supported in the rear of the frame 15. The brush roll 16 and the driving roll 18 are in parallel to each other. The brush roll 16 is composed of a tire 16B and bristle 16A having a longer diameter than the tire 16B. The driving roll 18 has an elastic surface. For example, a silicone roll is used as the driving roll 18. The driving roll 18 may have ribs on its surface.

The adhesive roll 21 is disposed to bridge the distance between the brush roll 16 and the driving roll 18 and rotates on its axis accompanying the rotation of the brush roll 16 and the driving roll 18. There is an opening in the upper part of the frame 15, through which the adhesive roll 21 is loaded and unloaded. The opening is covered with a removable transparent cover 22.

A dust scooper 23 is supported at the back of the brush roll 16 in the frame 15. The dust scooper 23 has a bottom 23A, which is brought into contact with flooring and a scoop 23B having a curved or flat surface which faces the brush roll 16 with or without a clearance. The dust scooper 23 has a flat projection 23C on both ends thereof and is vertically movably attached to both sides of the frame 15 with the projections 23C engaged with each rectangular hole 24 of the frame 15 which slants backward from the vertical. The dust scooper 23 is adapted to move upward with the projections 23C sliding up in the rectangular holes 24 and downward by its own weight so that the bottom 23A and the front edge of the scoop 23B always come into contact with flooring. As a result, all the dust scraped by the bristle 16A of the brush roll 16 can be guided to the adhesive roll 21 by the scoop 23B, without fail.

The cleaning operation with the cleaning tool 10 is carried out as follows. (1) A force is applied in the axial direction of the handle 11 to move the cleaning tool 10 forward on a floor to thereby rotate the tire 16B of the brush roll 16 and the driving roll 18. The adhesive roll cleaner 21 in contact with the driving roll 18 also rotates. (2) Dust is scraped off the floor by the bristle 16A of the brush roll 16, guided by the scoop 23B of the dust scooper 23 to the adhesive roll 21, and adhered to the rotating adhesive roll 21. (3) The dust adhered to the rotating adhesive roll 21 is carried to the driving roll 18, pressed by the driving roll 18 and secured to the adhesive surface of the adhesive roll 21. (4) After the adhesive surface of the adhesive roll 21 is saturated with dust, which can be visually confirmed through the transparent cover 22, the cover 22 is opened to taken out the adhesive roll 21 out. The outermost soiled adhesive sheet is then peeled off to expose a fresh adhesive surface. The adhesive roll is again set on the brush roll 16 and the driving roll 18, and the cover 22 is closed. Because the cleaning tool 10 is capable of moving back and forth, the dust caught on the driving roll 18 is picked up by the adhesive roll 21 when moving backward. The rear edge of the bottom 23A of the dust scooper 23 is rounded so as to prevent the rear edge from being caught up by the floor.

Figure 5:
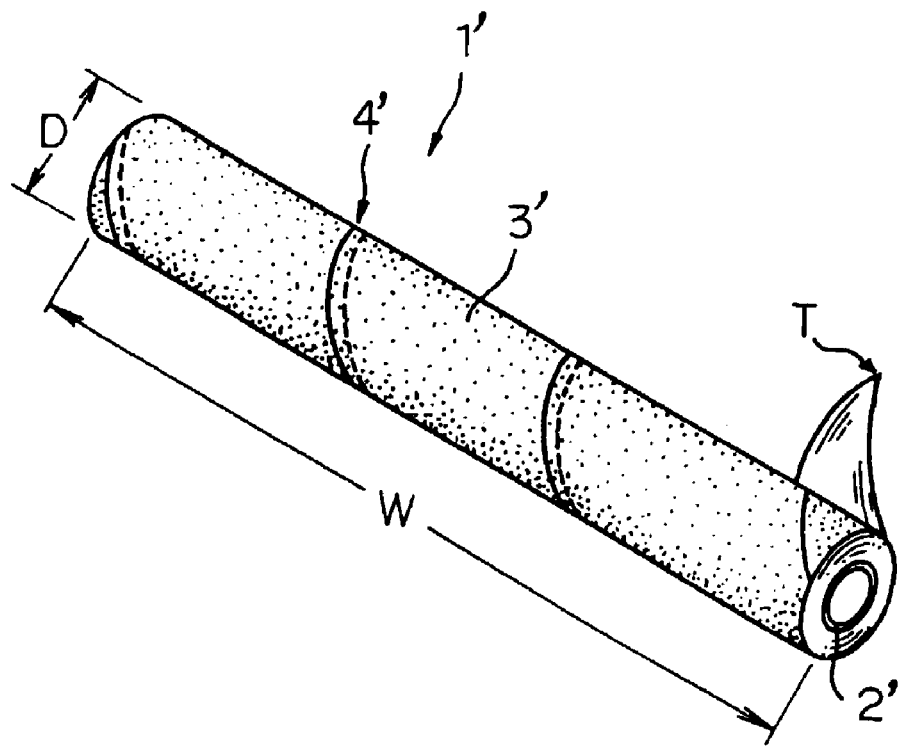
FIG. 5 is a perspective view of another embodiment of the adhesive roll cleaner according to the present invention.

The present invention is not limited to the above-described embodiment. For example, while in the embodiment described, the adhesive sheet 3 is wound around the core tube 2 with the edges even for every turn, an adhesive sheet 3' in the form of a wide tape may be helically wound around a core tube 2' with the adhesive surface facing out and with laps 4' between adjacent turns as illustrated in FIG. 5. The laps 4' make a level difference, which facilitates picking up the sharp-pointed tip T of the adhesive sheet 3' to start peeling a soiled adhesive sheet.

While the roll cleaner 1 shown in FIG. 1 has a perforated adhesive sheet of continuous length wound around the core tube, a prescribed number of cut adhesive sheets may be wound around the core in layers to make an adhesive roll cleaner of the invention.

The present invention will now be illustrated in greater detail with reference to Examples. The following Examples are presented as being exemplary of the present invention and should not be construed as limiting.

EXAMPLE 1

Bleached extensible kraft paper of continuous length (available from Oji Paper Co., Ltd.; basis weight: 75 g/m$^2$) was laminated with a 15 μm thick polyethylene film, and a silicone release agent was applied to the polyethylene side to prepare a base sheet. The non-finished side of the base sheet was coated with 14 g/m$^2$ of a styrene-isoprene-styrene block copolymer (SIS) hot-melt adhesive to obtain a 195 mm wide single-sided adhesive sheet of continuous length. The adhesive sheet was wound around a paper core tube having an inner diameter of 25.4 mm (1 in.), a thickness of 1.4 mm, and an outer diameter of 28.2 mm with the adhesive side out to obtain an adhesive roll cleaner having an outer diameter of 35 mm and a width of 195 mm.

EXAMPLES 2 AND 3

An adhesive roll cleaner of 35 mm in outer diameter and 195 mm in width was prepared in the same manner as in Example 1, except for changing the coating weight of the SIS hot-melt adhesive to 23 g/m² (Example 2) or 32 g/m² (Example 3).

EXAMPLE 4

A side of bleached kraft paper of continuous length (available from Chuetsu Pulp & Paper Co., Ltd.; basis weight: 50 g/m²) was laminated with a 15 μm thick polyethylene film and coated with a silicone release agent. The opposite side of the paper was coated with 37 g/m² of an SIS adhesive to prepare a single-sided adhesive sheet. The adhesive sheet was wound around a paper core in the same manner as in Example 1 to obtain an adhesive roll cleaner of 35 mm in outer diameter and 195 mm in width.

COMPARATIVE EXAMPLE 1

A commercially available adhesive roll cleaner, Korokoro available from Nitoms Inc. was tested as such.

COMPARATIVE EXAMPLE 2

The same adhesive roll cleaner as used in Comparative Example 1 (Korokoro) was tested after the adhesive sheet was unwound and removed to reduce its outer diameter to 35 mm. The width of the cleaner was 160 mm.

COMPARATIVE EXAMPLE 3

A commercially available adhesive roll cleaner, Mrs. Roll available from Sekisui Life-Tec Co., Ltd. was tested as such.

COMPARATIVE EXAMPLE 4

The same adhesive roll cleaner as used in Comparative Example 3 (Mrs. Roll) was tested after the adhesive sheet was unwound and removed to reduce its outer diameter to 35 mm. The width of the cleaner was 160 mm.

Evaluation of Performance:

The adhesive roll cleaners of Examples and Comparative Examples were measured for dimensions (outer diameter D and width W), rolling ball tack, and Elmendorf tear strength (in MD) according to the methods previously described. Further, cleaning performance under a small clearance and hair collecting performance of each adhesive roll cleaner and peelability of the adhesive sheet entwined with hairs were evaluated in accordance with the methods described below. The results obtained are shown in Table 1.

1) Cleaning Performance Under Small Clearance

Figure 6:
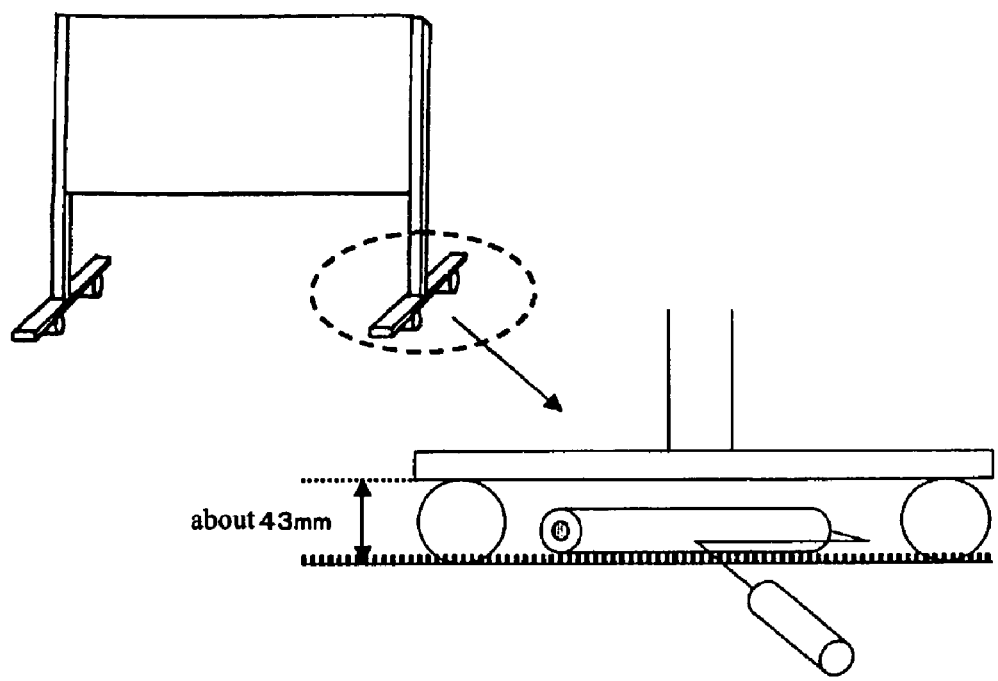
FIG. 6 illustrates a method of evaluating cleaning performance in a narrow space.

A castered electronic white board (Panaboard UB-1280, supplied by Matsushita Graphic Communication Systems Inc.) was placed on a cut pile carpet (San Harmony, available from Sangetsu Co., Ltd.; made of 85% acrylic fiber and 15% nylon fiber; pile length: 8 mm; gauge: 1/10"; stitch per inch: 14.5). The casters were 50 mm high, and the clearance between the castered (raised) base and the carpet was 43 mm high (see FIG. 6). The roll cleaner was attached to the cleaning tool shown in FIG. 2 and rolled under the raised base to clean the carpet. The outer diameter of the roll cleaner is shown in Table 1. The commercially available adhesive rolls of Comparative Examples 1 and 3 were used in mint condition, removed from the package. Cleaning performance was rated "pass (P)" or "failure (F)" as follows.

P: The roll cleaner passes through the clearance under the raised base and smoothly cleans the carpet.

F: The roll cleaner does not pass through the clearance under the raised base and fails to clean the carpet smoothly.

2) Hair Collecting Performance

The hair collecting performance of the roll cleaners which were (A) unsoiled or (B) somewhat soiled was evaluated.

(A) A cut pile carpet (San Harmony, available from Sangetsu Co., Ltd.; made of 85% acrylic fiber and 15% nylon fiber; pile length: 8 mm; gauge: 1/10"; stitch per inch: 14.5) was cleaned with a vacuum cleaner equipped with a rotating brush in a "carpet mode". Ten human hairs of 10 cm in length were scattered uniformly over an area of 50 cm by 50 cm of the vacuumed carpet. The adhesive roll cleaner containing no dust was attached to each of a direct contact type cleaning tool shown in FIG. 2 and an indirect contact type cleaning tool shown in FIGS. 3 and 4. The cleaning tool was rolled on that area of the carpet back and forth 5 times (5 double strokes). A percentage of the number of the hairs caught on the adhesive sheet to the total number of scattered hairs (10) was calculated as a measure of hair collecting performance. The test was carried out three times to obtain an average percentage.

(B) 100% Acrylic yarn (fiber diameter: 20 to 25 μm) was cut to 1 to 2 mm lengths and unraveled to prepare simulated dust. The same test as in (A) was performed except that the roll cleaner had previously been soiled by uniformly applying 0.065 g of the simulated dust to the adhesive surface.

Figure 7:
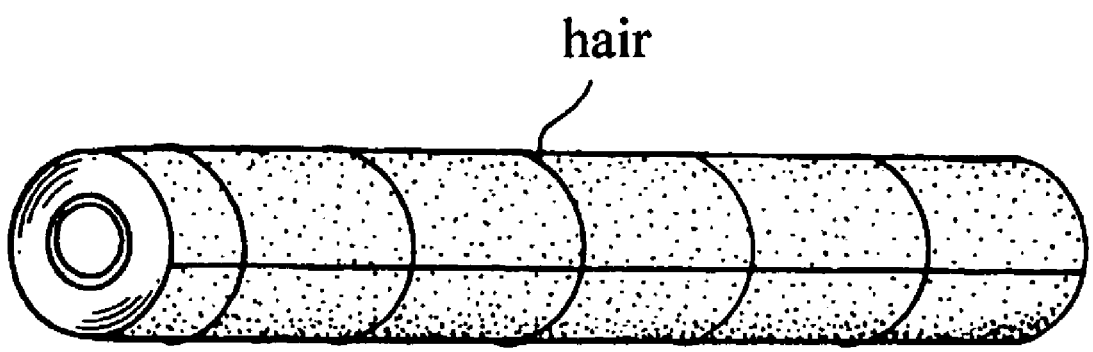
FIG. 7 is a perspective view of a roll cleaner entwined with hairs, which is used to evaluate peelability of an adhesive sheet.

3) Peelability of Adhesive Sheet Entwined with Hairs:

Five human straight hairs of 10 cm in length and 70 to 100 μm in diameter were coiled around the adhesive roll at 20 to 30 mm intervals in the width direction of the roll as illustrated in FIG. 7. The adhesive roll was attached to a J-roll holder (supporting axis diameter: 24 mm or 37 mm) shown in FIG. 2 and rolled back and forth 5 times (5 double strokes) on the same carpet as used above to firmly adhere the hairs to the adhesive sheet. The winding end at an edge of the adhesive sheet was picked between fingers, and the sheet was peeled off. The peelability of the adhesive sheet was rated based on the following standard.

A: The adhesive sheet was easily peeled without being torn.

B: The adhesive sheet was torn by the hairs and difficult to peel.

TABLE 1

| | | Example | | | | Comparative Example | | | |
|---|---|---|---|---|---|---|---|---|---|
| | | 1 | 2 | 3 | 4 | 1 | 2 | 3 | 4 |
| Roll Cleaner | Outer Diameter D (mm) | 35 | 35 | 35 | 35 | 56 | 35 | 54 | 35 |
| | Width W (mm) | 195 | 195 | 195 | 195 | 160 | 160 | 160 | 160 |
| | Rolling Ball Tack | 11 | 14 | 20 | 20 | 13 | 13 | 10 | 10 |

TABLE 1-continued

|  | Example | | | | Comparative Example | | | |
| --- | --- | --- | --- | --- | --- | --- | --- | --- |
|  | 1 | 2 | 3 | 4 | 1 | 2 | 3 | 4 |
| Adhesive Coating Weight (g/m$^2$) | 14 | 23 | 32 | 37 | — | — | — | — |
| Elmendorf Tear Strength (mN) | 870 | 870 | 870 | 520 | 265 | 265 | 260 | 260 |
| Cleaning Performance under Small Clearance | P | P | P | P | F | P | F | P |
| Hair Collecting Performance* A (direct contact) | 100 | 100 | 100 | 100 | 100 | 100 | 100 | 100 |
| B (direct contact) | 100 | 100 | 100 | 100 | 100 | 100 | 10 | 0 |
| A (indirect contact) | 100 | 100 | 100 | 100 | unattachable to the cleaning tool | | | |
| B (indirect contact) | 40 | 40 | 70 | 70 | | | | |
| Peelability | A | A | A | A | B | B | B | B |

*A: Unsoiled; B: Soiled with 0.065 g of cut fiber

As is apparent from the results shown in Table 1, the roll cleaners of Examples are superior to the comparative ones in cleaning performance under small clearance and exhibit high hair collecting performance. It is also seen that the adhesive sheet of the roll cleaners of the Examples is prevented from being torn by twining hairs when peeled.

As described above, the adhesive roll cleaner of the present invention is compact and manageable in size sufficient to catch dust from a floor under furniture with a raised base, such as castered furniture or at corners of a room between walls and the floor and yet exhibits satisfactory dust collecting performance and satisfactory cleaning performance sustainability. Where the adhesive sheet has an Elmendorf tear strength in the specific range, it is prevented from being torn by a hair, etc. twining therearound. Where the adhesive sheet has a rolling ball tack in the specific range, the roll cleaner exhibits capability of collecting a sufficient amount of dust and satisfactory cleaning performance sustainability even though the outer diameter is reduced to reduce the area of the adhesive surface.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An adhesive roll cleaner having a single-sided adhesive sheet wound around a core tube into a roll with the adhesive side facing out,
    wherein said adhesive sheet has a tear strength of at least 500 mN and is wound in such a manner that the adhesive roll cleaner maintains an outer diameter and width from start to end of use which renders it effective for cleaning in small clearance spaces,
    wherein the adhesive sheet has a rolling ball tack of 11 to 30,
    wherein the adhesive sheet comprises a base sheet comprising paper containing soft wood pulp having a long fiber length or made from wood pulp mixed with glass fiber or synthetic rubber,
    wherein the base sheet has a basis weight of 40 to 200g/m$^2$,
    wherein the adhesive of the adhesive sheet comprises a hot-melt adhesive, solvent adhesive or aqueous adhesive,
    wherein the adhesive is applied to the base sheet at a coating weight of 15 to 50 g/m$^2$,
    wherein a silicone release agent is applied to a back side of the adhesive sheet,
    and wherein the adhesive roll maintains an outer diameter within a range of 22 to 40 mm from start to end of use and the roll has a width of 180 to 300 mm.

2. A cleaning tool which contains the adhesive roll cleaner of claim 1, said adhesive roll cleaner being mounted on a roller having a diameter of 20 to 30 mm and a width of 180 to 300 mm.

3. A cleaning tool comprising a frame member containing a brush roll and a driving roll rotatably mounted therein, and the adhesive roll cleaner according to claim 1.

4. The cleaning tool according to claim 3, comprising a single adhesive roll cleaner.

* * * * *